(12) United States Patent
Armand et al.

(10) Patent No.: US 9,737,687 B2
(45) Date of Patent: Aug. 22, 2017

(54) CABLE-DRIVEN MORPHABLE MANIPULATOR

(75) Inventors: Mehran Armand, Maple Lawn, MD (US); Michael D. Kutzer, Baltimore, MD (US); Christopher Y. Brown, Olney, MD (US); Russell H. Taylor, Severna Park, MD (US); Ehsan Basafa, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 33 days.

(21) Appl. No.: 13/825,461

(22) PCT Filed: Sep. 22, 2011

(86) PCT No.: PCT/US2011/052728
§ 371 (c)(1),
(2), (4) Date: Mar. 21, 2013

(87) PCT Pub. No.: WO2012/040442
PCT Pub. Date: Mar. 29, 2012

(65) Prior Publication Data
US 2013/0197306 A1    Aug. 1, 2013

Related U.S. Application Data

(60) Provisional application No. 61/385,168, filed on Sep. 22, 2010, provisional application No. 61/479,625, filed on Apr. 27, 2011.

(51) Int. Cl.
*A61B 1/00* (2006.01)
*A61M 25/00* (2006.01)
*A61M 25/01* (2006.01)
*A61B 1/005* (2006.01)
*A61B 17/34* (2006.01)
*A61B 18/22* (2006.01)
*A61B 17/00* (2006.01)
*A61B 17/29* (2006.01)

(52) U.S. Cl.
CPC ....... *A61M 25/0147* (2013.01); *A61B 1/0055* (2013.01); *A61B 1/0057* (2013.01);
(Continued)

(58) Field of Classification Search
CPC ..... A61B 1/005; A61B 1/0055; A61B 1/0057; A61B 1/0058; A61B 1/0071;
(Continued)

(56) References Cited

U.S. PATENT DOCUMENTS 4,329,980 A * 5/1982 Terada .......................... 600/140
5,235,964 A * 8/1993 Abenaim ...................... 600/139
(Continued)

FOREIGN PATENT DOCUMENTS

DE    2820239    11/1978
EP    1046406    10/2000
(Continued)

Primary Examiner — Timothy J Neal
Assistant Examiner — Aaron B Fairchild
(74) Attorney, Agent, or Firm — Noah J. Hayward

(57) ABSTRACT

A device includes first and second sheets of first and second elastic materials, respectively, and a control wire. The first sheet has a first thickness and a first length and is shaped to have a first cross-section having a first inner periphery and a first outer periphery. The second sheet has a second thickness and a second length and is shaped to have a second cross-section having a second inner periphery and a second outer periphery. One of the first sheet and the second sheet has a spacing disposed in along one of the first length and the second length, respectively. The first outer periphery is less than or equal to the second inner periphery. The second sheet surrounds the first sheet. The control wire has an end constrained to one of the first sheet the first material and the second sheet. The control wire is disposed within the spacing.

18 Claims, 13 Drawing Sheets

(52) U.S. Cl.
CPC ........ *A61B 1/0058* (2013.01); *A61B 17/3421* (2013.01); *A61M 25/0009* (2013.01); *A61B 2017/00309* (2013.01); *A61B 2017/00327* (2013.01); *A61B 2017/00867* (2013.01); *A61B 2017/2929* (2013.01); *A61B 2018/2238* (2013.01); *Y10T 29/49826* (2015.01)

(58) Field of Classification Search
CPC . A61B 2017/00867; A61B 2018/2238; A61M 25/0138; A61M 25/138; A61M 2205/0266
USPC ..... 600/139, 140, 143, 146, 151; 604/95.01, 604/95.04, 264, 528
See application file for complete search history.

(56) References Cited

U.S. PATENT DOCUMENTS

| | | | |
|---|---|---|---|
| 5,259,366 A * | 11/1993 | Reydel et al. | 600/124 |
| 5,325,845 A * | 7/1994 | Adair | A61B 1/0055 600/114 |
| 6,645,218 B1 | 11/2003 | Cassidy et al. | |
| 6,875,219 B2 | 4/2005 | Arramon et al. | |
| 6,949,106 B2 | 9/2005 | Brock et al. | |
| 7,226,467 B2 * | 6/2007 | Lucatero et al. | 606/213 |
| 7,837,674 B2 | 11/2010 | Cooper | |
| 7,862,580 B2 | 1/2011 | Cooper et al. | |
| 2003/0023142 A1 * | 1/2003 | Grabover | A61B 1/00071 600/143 |
| 2009/0137875 A1 * | 5/2009 | Kitagawa | A61B 1/0052 600/146 |
| 2010/0280525 A1 * | 11/2010 | Alvarez et al. | 606/130 |
| 2010/0312279 A1 | 12/2010 | Gephart et al. | |

FOREIGN PATENT DOCUMENTS

| | | |
|---|---|---|
| EP | 1083832 | 1/2009 |
| FR | 2645354 | 10/1990 |
| WO | 94/17856 | 8/1994 |
| WO | 99/62409 | 12/1999 |
| WO | 2010001114 | 1/2010 |
| WO | 2010/127162 | 11/2010 |

* cited by examiner

000# CABLE-DRIVEN MORPHABLE MANIPULATOR

CROSS-REFERENCE TO RELATED APPLICATIONS

This application claims priority to and the benefit of prior-filed U.S. Provisional Application Nos. 61/385,168 and 61/479,625, filed Sep. 22, 2010 and Apr. 27, 2011, respectively, the contents of which are herein incorporated by reference in their entireties.

BACKGROUND

Technical Field

The present invention generally relates to manipulator devices and, more particularly, to dexterous manipulators for use in minimally-invasive surgical procedures, for example.

Related Art

Snake-like dexterous manipulators (DMs) have found a variety of applications in robotic surgery in general and, specifically, in minimally-invasive surgery (MIS). The hyper-redundant dexterous manipulators used for MIS are designed for such uses as carrying diagnostic tools (e.g., for endoscopic and arthroscopic surgery), palpating tumors, suturing soft tissue, needle-steering (e.g., for micro and neurosurgery), micro-grasping in fetal surgery, gastro-intestinal interventions, and ENT (ear, nose, and throat) surgeries, for example. These DMs typically assist surgeons in diagnosis and/or operating in constrained environments. The current generation of DMs lack structural stability, such as to withstand high external end-effector forces occurring in many applications, including orthopaedics, for example.

What is needed is an improved device and method for performing minimally-invasive surgical procedures.

SUMMARY

Embodiments of the present invention include, but are not limited to, a system for inserting and controlling a manipulator device within a human body and a method for fabricating the manipulator device.

In accordance with an embodiment of the present invention, a device includes a first sheet of a first material having elasticity, a second sheet of a second material having elasticity and a control wire. The first sheet of the first material has a first thickness and a first length and is shaped so as to have a first cross-section having a first inner periphery and a first outer periphery. The second sheet of the second material has a second thickness and a second length and is shaped so as to have a second cross-section having a second inner periphery and a second outer periphery. One of the first sheet of the first material and the second sheet of the second material has a spacing disposed in along one of the first length and the second length, respectively. The first outer periphery is less than or equal to the second inner periphery. The second sheet of the second material surrounds the first sheet of the first material. The control wire has an end constrained to one of the first sheet of the first material and the second sheet of the second material. The control wire is disposed within the spacing.

Additional advantages and novel features of the invention are set forth in part in the description which follows, and in part will become apparent to those skilled in the art upon examination of the following or may be learned by practice of the invention. The advantages of the invention may be realized and attained by means of the instrumentalities and combinations particularly pointed out in the appended claims. In addition, additional apparatus, system and method embodiments, for example, will become apparent from the following detailed description.

BRIEF DESCRIPTION OF THE DRAWINGS/FIGURES

The accompanying drawings, which are incorporated in and form a part of the specification, illustrate at least one exemplary embodiment of the present invention and, together with the description, describe the present invention. In the drawings.

DETAILED DESCRIPTION

In accordance with one or more of the present invention, a system enables retrieval of information and performance of procedures located within an entity (e.g., within a human body). Furthermore, the system provides a manipulator device for insertion into the entity for aiding in retrieval of information and performance of procedures.

The system includes a Graphical User Interface (GUI) for performing viewing of information associated with system and with internal portions (e.g. body tissue) of the entity. Furthermore, the system provides an input interface (e.g.

joystick) for communication information to system. The system additionally provides a processor for receiving and processing information associated with system. The system additionally provides a controller device for applying forces to control wires associated with a manipulator device. Furthermore, application of forces to control wires associated with the manipulator device facilitates bending or flexing of manipulator device. Still further, the system provides an instrument portion for receiving information from manipulator device (e.g. images) and for providing instruments for performing procedures internal to entity. Still further, instruments may be inserted into the entity via a cavity traversing the length of the manipulator device.

As a non-limiting example, the manipulator device is inserted into a human body via an incision in the body. The manipulator device may be bent or flexed in order to present instruments to a desired location within the human body. Images of portions of the inside of the human body may be viewed via an optical device inserted into the body by way of a cavity located within manipulator device. A surgical procedure may be performed by instruments inserted into the human body by way of the manipulator device.

Additional example embodiments of the present invention will now be described in greater detail with reference to FIGS. 1-9.

Figure 1A:
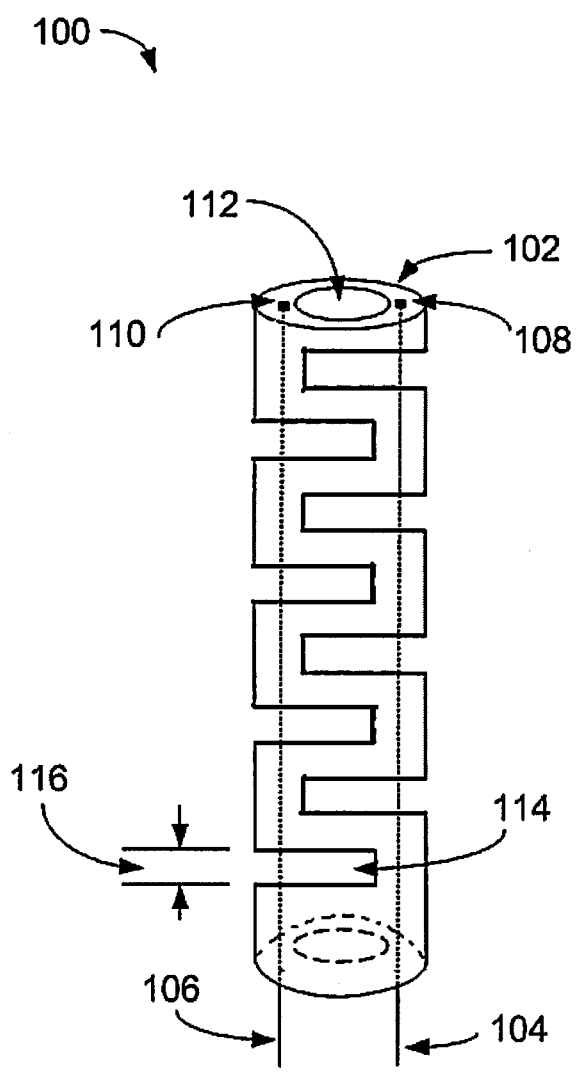
FIG. 1A is an illustration for an example manipulator device, in accordance with an embodiment of the present invention.

FIG. 1A is an illustration for an example manipulator device 100, in accordance with an exemplary embodiment of the present invention.

Manipulator device 100 includes a tube assembly 102, a control wire 104, a control wire 106, a termination device 108 and a termination device 110.

Control wire 104 is arranged to traverse from below right portion of tube assembly 102 to the top right portion of tube assembly 102. Control wire 106 is arranged to traverse from below left portion of tube assembly 102 to the top left portion of tube assembly 102.

Control wire 104 is constrained to the top of tube assembly 102 via termination device 108. Control wire 106 is constrained to the top of tube assembly 102 via termination device 110.

A tubular cavity 112 traverses from the bottom of tube assembly 102 to the top of tube assembly 102. A plurality of notches are staggered internal to tube assembly 102 with a sampling denoted as a notch 114. Notch 114 has a height dimension noted as a height dimension 116.

In a preferred embodiment, the tube assembly 102 is constructed of an elastic material. Furthermore, elastic material may have shape memory. Shape memory is a characteristic where an alloy remembers an original, cold-forged shape. Additionally, the material may return to its pre-deformed shape via heating. As a non-limiting example, tube assembly 102 may be fabricated of nitinol. Nitinol is a metal alloy including nickel and titanium, where these two elements are roughly in equal atomic percentages.

Control wires 104 and 106 may be constructed of any bendable material that resists stretching along its length, non-limiting examples of which include metal, cloth and plastic.

Termination device 108 and termination device 110 may be any system or device that is able to constrain the end of control wire 104 and the end of control wire 106, respectively, to an end of tube assembly 102.

In one or more embodiments, termination devices 108 and 110 fix the end of control wire 104 and the end of control wire 106, respectively, to an end of tube assembly 102. Non-limiting examples of such fixing termination devices include: holes provided at the end of tube assembly 102 into which the end of control wire 104 and the end of control wire 106 may be tied; soldering the end of control wire 104 and the end of control wire 106 to the end of tube assembly; and gluing the end of control wire 104 and the end of control wire 106 to the end of tube assembly.

In one or more embodiments, termination devices 108 and 110 prevent the end of control wire 104 and the end of control wire 106, respectively, from being pulled away from the end of tube assembly 102. For example, holes may be provided at the end of tube assembly 102 into which the end of control wire 104 and the end of control wire 106 may inserted. A retaining mechanism may be used to prevent the end of control wire 104 and the end of control wire 106 from being pulled back through the holes at the end of tube assembly 102. Non-limiting examples of retaining mechanisms include: soldering a bead onto the end of control wire 104 and the end of control wire 106; gluing a bead onto the end of control wire 104 and the end of control wire 106; and tying knots at the end of control wire 104 and the end of control wire 106.

Manipulator device 100 enables the insertion of instruments and other devices into a body for medically associated applications. Any device may be inserted, so long as it fits within tubular cavity 112. Non-limiting examples of devices include imaging instruments, cauterizing instruments, cutting instruments and material delivery instruments. For example, a person may require removal of some body tissue. Manipulator device 100 may be inserted into a minimal incision on person's body. Once inside, manipulator device 100 may be continuously inserted, spun and/or bent in order to easily position the surgical device or devices for cutting and removing the appropriate body tissue.

Control wire 104 enables bending and unbending tube assembly 102 to/from the right direction of manipulator device 100. Control wire 106 enables bending and unbending tube assembly 102 to/from the left direction of manipulator device 100.

Termination device 108 secures control wire 104 such that force may be applied to control wire 104 in order to flex and un-flex tube assembly 102. Termination device 110 secures control wire 106 such that force may be applied to control wire in order to flex and un-flex tube assembly 102.

Notches, for example notch 114, assist manipulator device 100 to bend. When manipulator device 100 is not bent, height dimension 116 associated with notch 114 is uniform throughout the width and breadth of notch 114. When manipulator device 100 is bent, then height dimension 116 is not uniform throughout the width and breadth of notch 114.

In operation, manipulator device 100 is inserted into a body, such as a human body, although additional exemplary embodiments are not limited thereto. Manipulator device 100 may be bent or unbent as a result of the flexible nature of materials used for constructing manipulator device 100 and as a result of the notches (e.g. notch 114). The amount of flexing for manipulator device 100 is controlled via control wire 104 and control wire 106. The flexing or bending of manipulator device 100 is controlled via the application and removal of force to control wire 104 and/or control wire 106. A medical device traverses through the lower entry of tubular cavity 112 and exits through the upper entry of tubular cavity 112. The medical device may be used to perform a medical procedure.

Figure 1B:
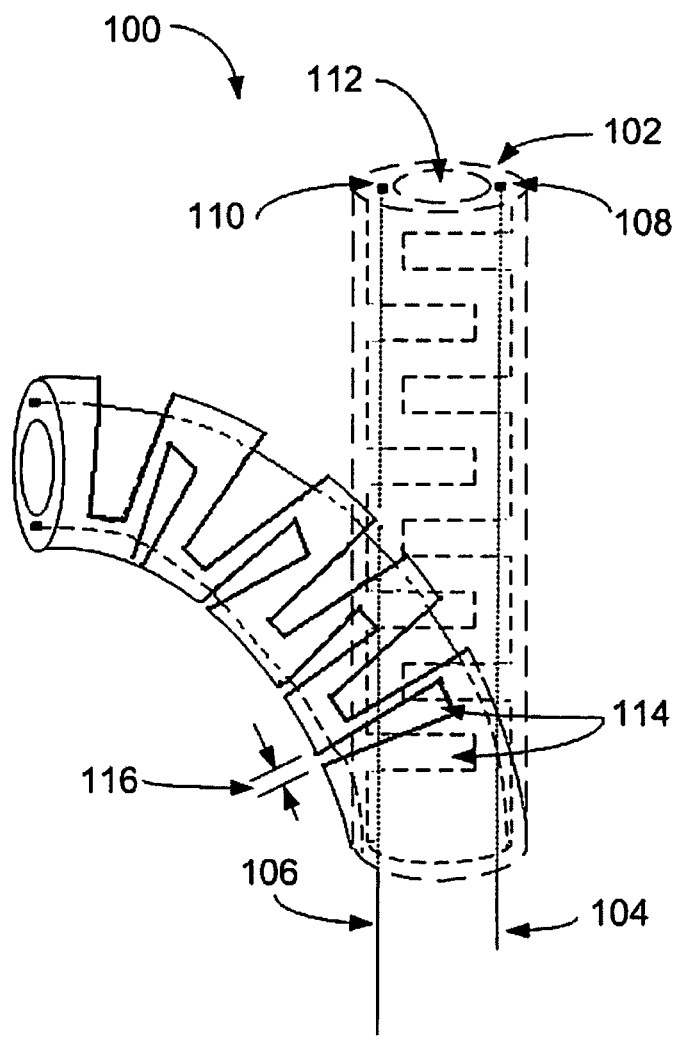
FIG. 1B is an illustration for bending the example manipulator device as described with reference to FIG. 1A, in accordance with an embodiment of the present invention.

FIG. 1B is an illustration for bending the example manipulator device as described with reference to FIG. 1A, in accordance with an exemplary embodiment of the present invention.

As shown in FIG. 1B, a downward force has been applied to control wire 106 for pulling a portion of control wire 106 out of manipulator device 100. The application of the downward force to control wire 106 bends manipulator device 100 to the left. As a result of the bending, height dimension 116 is smaller in FIG. 1B than in FIG. 1A. Furthermore, height dimension 116 in FIG. 1B is not uniform about the width and breadth of notch 114, as described with reference to FIG. 1A. The smaller height of height dimension 116 in FIG. 1B as compared to FIG. 1A aids in the amount of flexibility associated with manipulator device 100.

As an example, manipulator device 100 may be configured as in FIG. 1B for performing a medical procedure to some body tissue located to the left of manipulator device 100, but requires flexing or bending in order to reach the body tissue.

Removal of the downward force applied to control wire 106 returns manipulator device 100 to the configuration as described with reference to FIG. 1A.

Figure 1C:
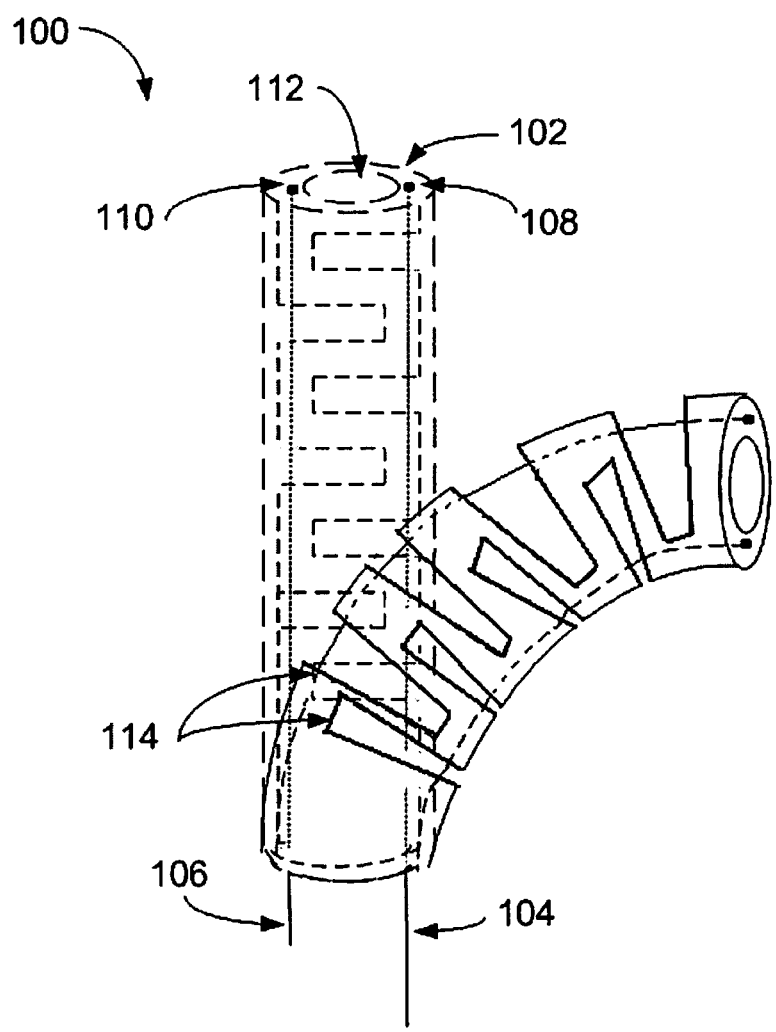
FIG. 1C is an illustration for bending the example manipulator device as described with reference to FIG. 1A, in accordance with an embodiment of the present invention.

FIG. 1C is an illustration for bending the example manipulator device as described with reference to FIG. 1A, in accordance with an exemplary embodiment of the present invention.

As shown in FIG. 1C, a downward force has been applied to control wire 104 for pulling a portion of control wire 106 out of manipulator device 100. The application of the downward force to control wire 106 bends manipulator device 100 to the right.

Removal of the downward force applied to control wire 104 returns manipulator device 100 to the configuration as described with reference to FIG. 1A.

Figure 1D:
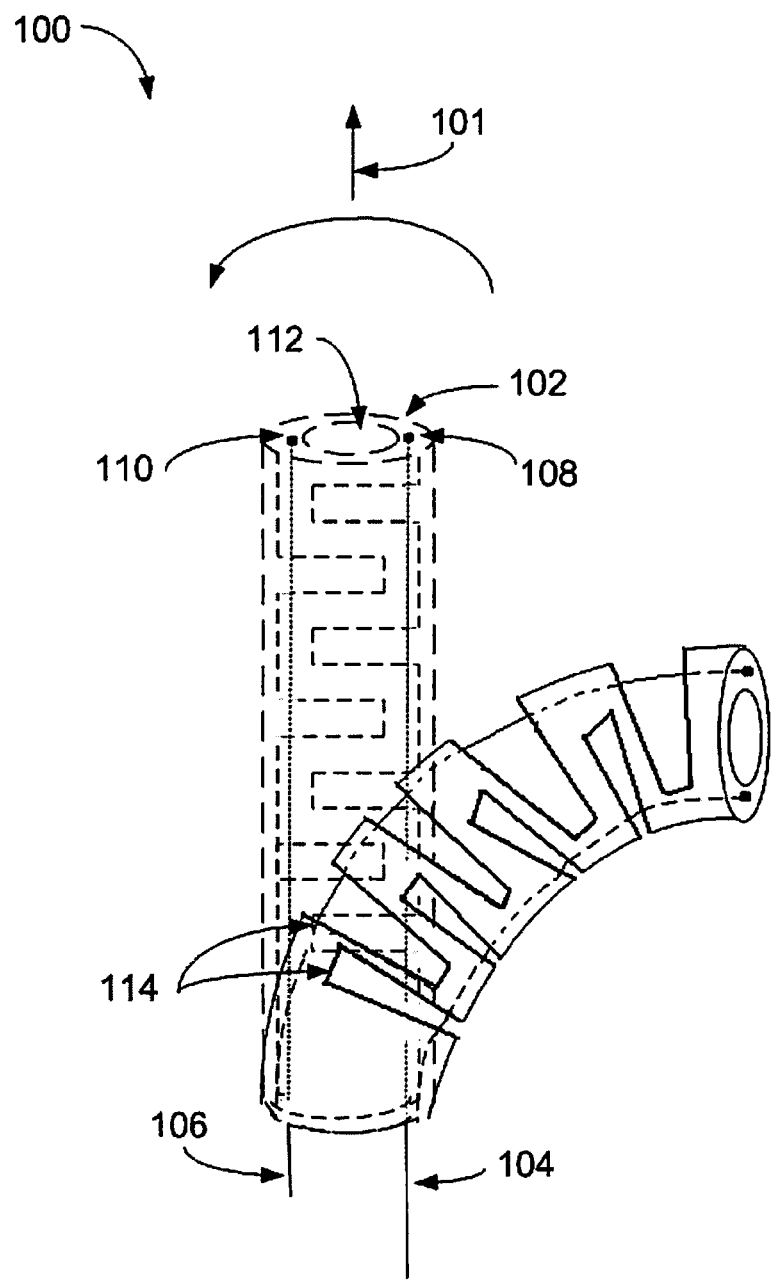
FIG. 1D is an illustration for rotating the example manipulator device as described with reference to FIGS. 1A-C, in accordance with an embodiment of the present invention.

FIG. 1D is an illustration for rotating the example manipulator device as described with reference to FIGS. 1A-C, in accordance with an exemplary embodiment of the present invention.

As shown in FIG. 1D, manipulator device 100 may be rotated about a y-axis 101. For example, a portion of body tissue may need to be examined located to the right and rear of manipulator device 100. Application of a downward force to control wire 104 enables bending of manipulator device 100 and counter-clockwise rotation of manipulator device 100 about y-axis 101 enables movement of the device towards the rear. The bending of manipulator device 100 in conjunction with counter-clockwise rotation of device enables examination of the body tissue located to the right and rear of manipulator device 100.

A plurality of control wires and associated terminating devices may be configured for enabling a wide range of flexibility options for manipulator device 100.

Figure 1E:
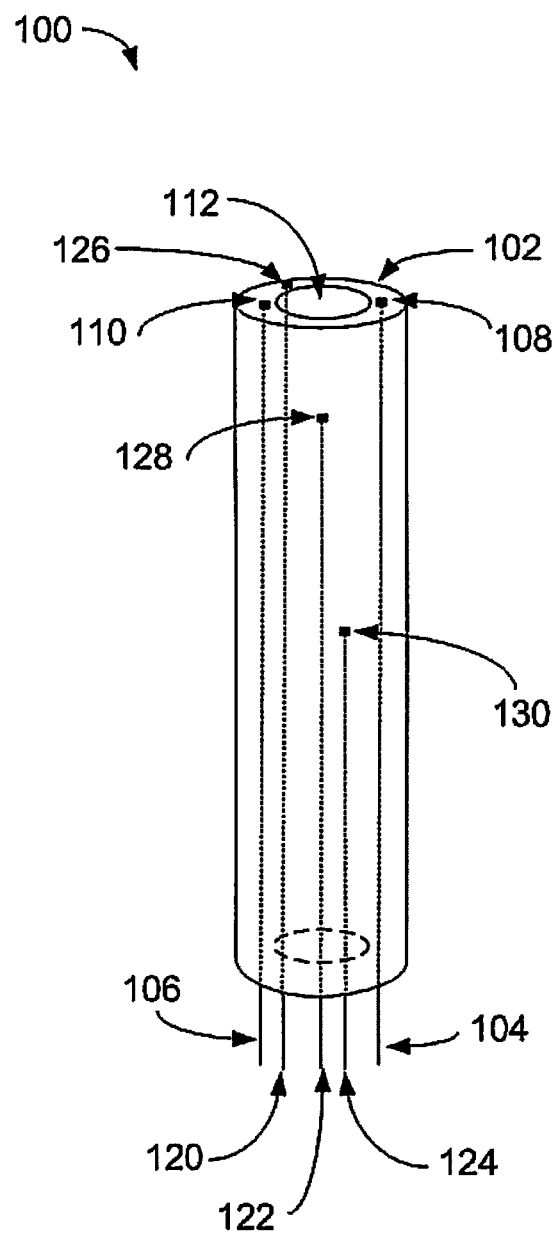
FIG. 1E is an illustration of the example manipulator device as described with reference to FIG. 1A with a multiplicity of control wires, in accordance with an embodiment of the present invention.

FIG. 1E is an illustration of the example manipulator device as described with reference to FIG. 1A with a plurality of control wires, in accordance with an exemplary embodiment of the present invention.

A control wire 120 traverses from the lower left rear portion of manipulator device 100 to the upper left rear portion of manipulator device 100. A control wire 122 traverses from the lower middle front portion of manipulator device 100 to the upper ¾ middle portion of manipulator device 100. A control wire 124 traverses from the lower right front portion of manipulator device 100 to near the front midpoint of manipulator device 100.

Control wire 120 is terminated via a termination device 126 located at the top right rear portion of manipulator device 100. Control wire 122 is terminated via a termination device 128 located at the upper ¾ middle portion of manipulator device 100. Control wire 124 is terminated via a termination device 130 located near the front midpoint of manipulator device 100.

Control wire 120 enables bending of manipulator device 100 towards the left rearward direction. Control wire 122 enables bending of manipulator device 100 towards the front of manipulator device 100. Control wire 124 enables bending manipulator device 100 towards the front of manipulator device 100.

The differing locations for the terminating devices enables varying amounts of bending associated with manipulator device 100. For example, control wire 104, control wire 106 and control wire 120 enable the entire length of manipulator device 100 to be bent when a downward force is applied to control wire 104, control wire 106 and control wire 120. As another example, application of a downward force to control wire 122 bends manipulator device 100 from termination device 128 and below, but manipulator device 100 does not bend above termination device 128.

The control wires and terminating devices may be configured in any known quantity and manner in order to allow for bending manipulator device 100 in a plethora of arrangements. Furthermore, a variety of downward forces may be applied to the multiplicity of control wires in order to aid in supplying a variety of arrangements.

Figure 2:
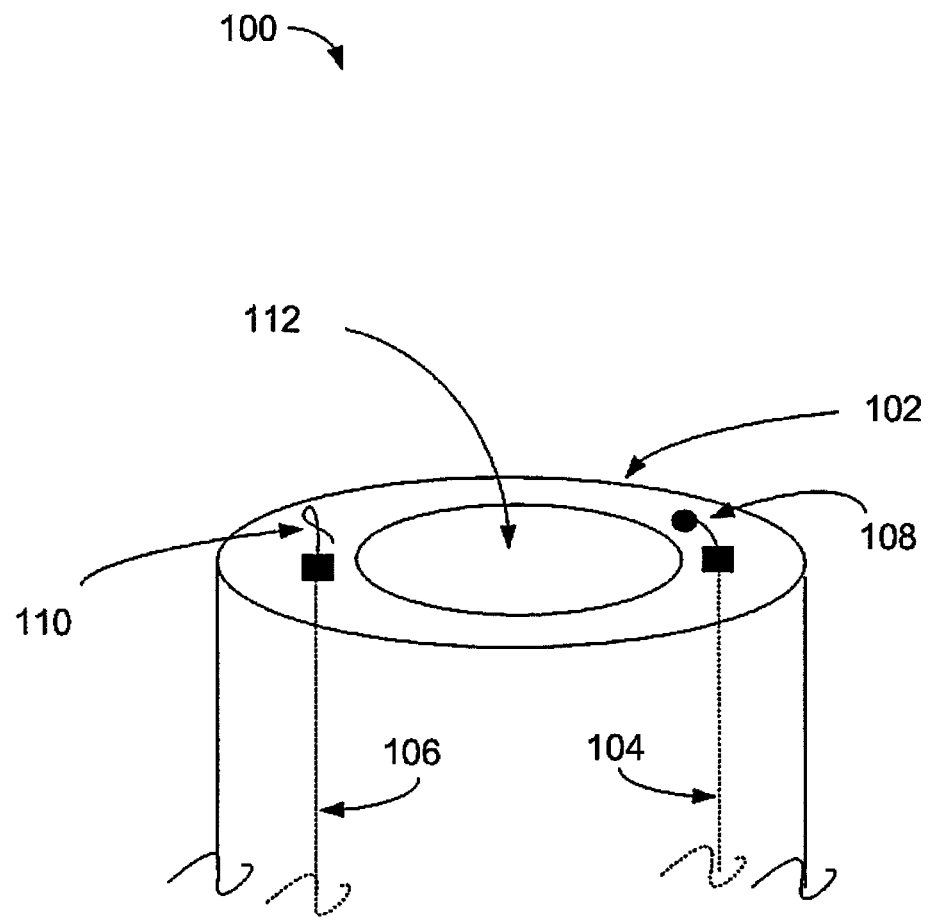
FIG. 2 is an illustration of the example control wire terminations for the manipulator device as described with reference to FIG. 1A, in accordance with an embodiment of the present invention.

FIG. 2 is an illustration of the example control wire terminations for the manipulator device as described with reference to FIG. 1A, in accordance with an exemplary embodiment of the present invention.

Control wires may be secured via any known system or method, non-limiting examples of which include a knot, a weld, solder and glue.

Termination device 108 is configured as securing control wire 104 via welding of control wire 104 to tube assembly 102. Termination device 110 is configured as a knot for securing control wire 106.

Figure 3:
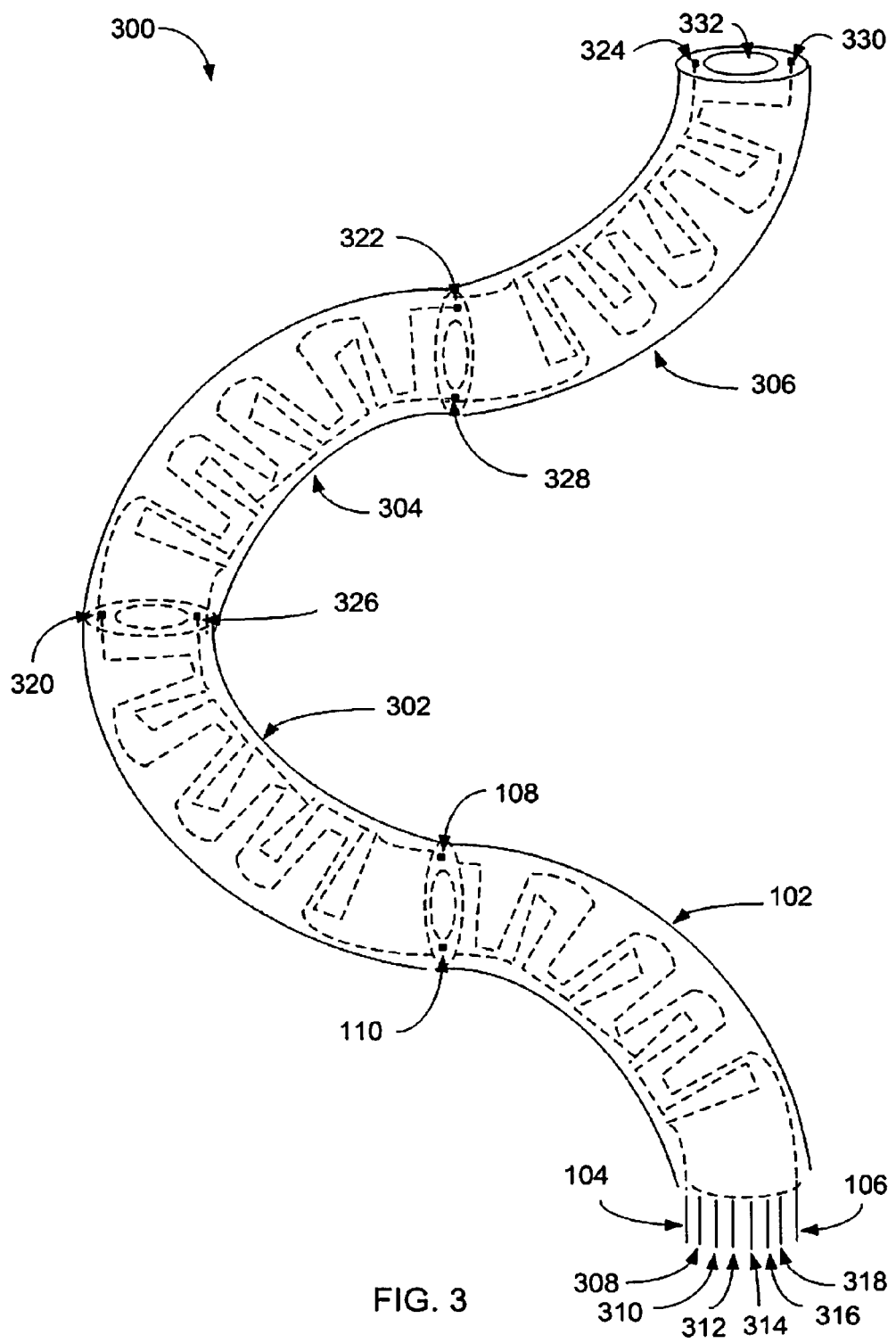
FIG. 3 is an illustration of an example manipulator device with a multiplicity of bends, in accordance with an embodiment of the present invention.

FIG. 3 is an illustration of an example manipulator device 300 with a plurality of bends, in accordance with an exemplary embodiment of the present invention.

Manipulator device 300 includes tube assembly 102, a tube portion 302, a tube portion 304, a tube portion 306 and control wires 308, 310, 312, 314, 316, and 318.

Control wires are arranged to enter a first end of tube assembly 102. A second end of tube assembly 102 is arranged to connect to a first end of tube portion 302. A second end of tube portion 302 is arranged to connect to a first end of tube portion 304. A second end of tube portion 304 is arranged to connect to a first end of tube portion 306.

Control wire 308 is arranged to traverse the left side of tube assembly 102 and tube portion 302. Furthermore, control wire 308 is secured via a termination device 320. Control wire 310 is arranged to traverse the left side of tube assembly 102, tube portion 302 and tube portion 304. Furthermore, control wire 310 is secured via a termination device 322. Control wire 312 is arranged to traverse the left side of tube assembly 102, tube portion 302, tube portion 304 and tube portion 306. Furthermore, control wire 312 is secured via a termination device 324. Control wire 314 is arranged to traverse the right side of tube assembly 102 and tube portion 302. Furthermore, control wire 314 is secured via a termination device 326. Control wire 316 is arranged to traverse the right side of tube assembly 102, tube portion 302 and tube portion 304. Furthermore, control wire 316 is secured via a termination device 328. Control wire 318 is arranged to traverse the right side of tube assembly 102, tube portion 302, tube portion 304 and tube portion 302. Furthermore, control wire 318 is secured via a termination device 330.

In a preferred embodiment, a tubular cavity 332 traverses the length of manipulator device 300. Tubular cavity 332 enables insertion of instruments through manipulator device 300 for performing functions located internal to an entity. As an example, a tissue located internal to a human body may need observation and an optical device may be inserted through tubular cavity 332 for performing the observation.

Tube portion 302, tube portion 304 and tube portion 306 perform a similar function as tube assembly 102 as described previously with reference to FIGS. 1A-1E and FIG. 2.

Applying a downward force to control wire 314 enables bending of tube portion 302 to the left as illustrated. Applying a downward force to control wire 310 enables bending of tube portion 304 to the right as illustrated. Applying a downward force to control wire 312 enables bending of tube portion 306 to the left as illustrated.

In operation, applying downward force to control wires 104, 308, 310, 312, 314, 316, 318 and 106 enable bend and unbending of manipulator device 300 in a variety of configurations. As an example, a tissue located internal to a human body may need observation requiring an instrument to be navigated around a multiplicity of structures (e.g. bones). By manipulating the forces applied to the control wires, manipulator device 300 may be flexed for navigating around the internal structures.

Figure 4:
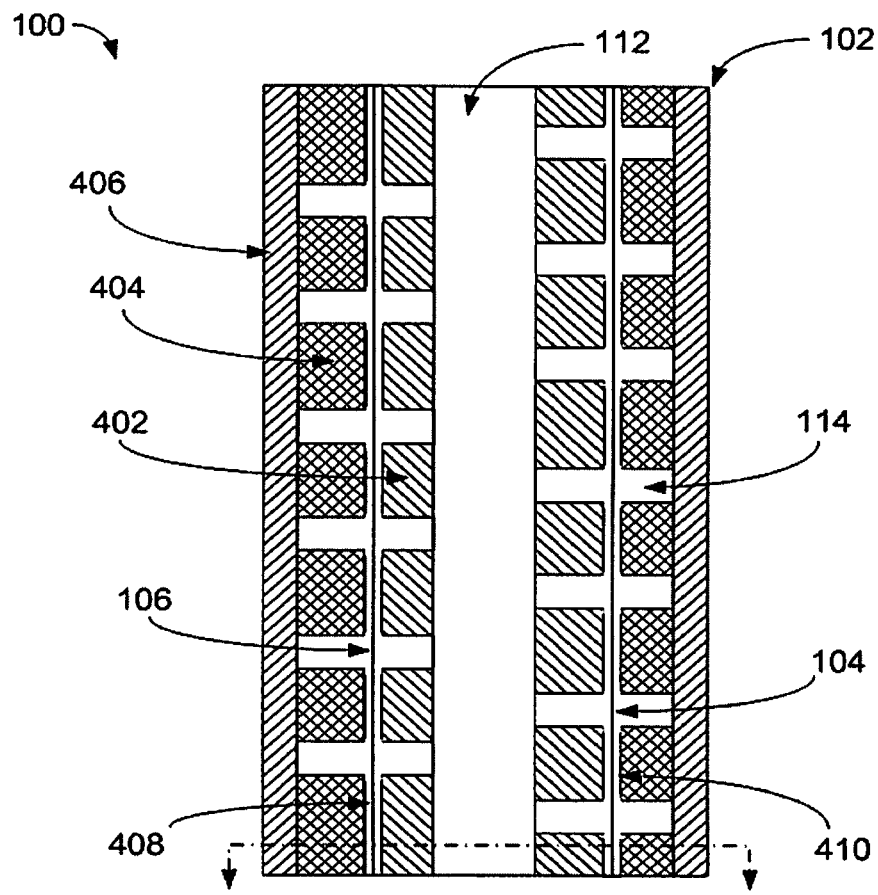
FIG. 4 is a cross-section illustration of example manipulator device as described with reference to FIG. 1A-E, in accordance with an embodiment of the present invention.
Figure 4:
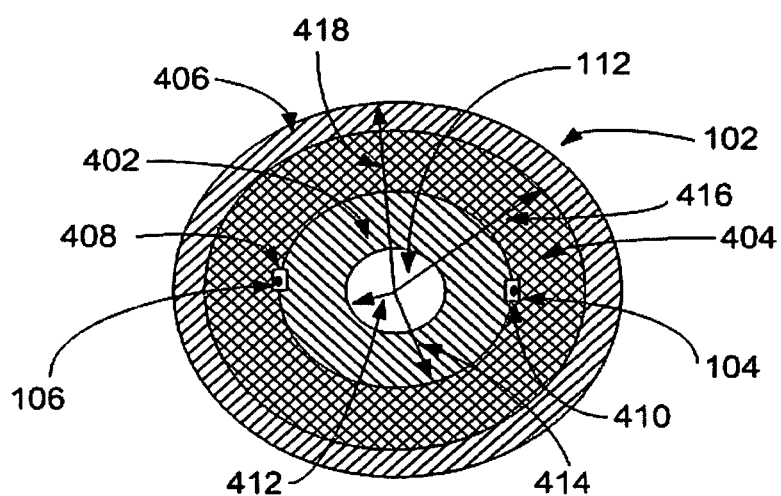

FIG. 4 is a cross-section illustration of example manipulator device as described with reference to FIG. 1A-E, in accordance with an exemplary embodiment of the present invention.

Tube assembly 102 includes an inner tube portion 402, an outer tube portion 404 and a tubular sheath portion 406. In a preferred embodiment, the inner tube portion 402 has a nominal inside diameter of 4 millimeters (mm) and a nominal outside diameter of 5 mm, while the outer tube portion 404 has a nominal inside diameter that is slightly smaller, e.g., by about 0.005 mm, than the 5 mm outside diameter of the inner tube portion 402 and a nominal outside diameter of 6 mm, although alternative exemplary embodiments are not limited to the foregoing diameters.

Inner tube portion 402 is arranged to surround tubular cavity 112. Outer tube portion 404 is arranged to surround inner tube portion 402. Tubular sheath portion 406 is arranged to surround outer tube portion 404. A spacing 408 is arranged on the left side of tube assembly 102 between inner tube portion 402 and outer tube portion 404. A spacing 410 is arranged on the right side of tube assembly 102 between inner tube portion 402 and outer tube portion 404. Control wire 104 is arranged within spacing 410. Control wire 106 is arranged within spacing 408.

The boundary between tubular cavity 112 and inner tube portion 402 is located at a radius 412. The boundary between inner tube portion 402 and outer tube portion 404 is located at a radius 414. The boundary between outer tube portion 404 and tubular sheath portion 406 is located at a radius 416. The outer radius for tubular sheath portion 406 is located at a radius 418.

A portion of spacing 408 is located greater than radius 414 within outer tube portion 404. Furthermore, a portion of spacing 408 is located less than radius 414 within inner tube portion 402. Notch 114 extends from radius 412 to radius 416.

Increasing and/or decreasing downward forces applied to control wire 104 and/or control wire 106 operate to bend or flex tube assembly 102. For equal lengths of control wire and control wire 106, a greater force applied to control wire 104 bends or flexes tube assembly 102 to the right. Furthermore, a greater force applied to control wire 106 bends or flexes tube assembly 102 to the left.

Tube assembly 102 may have any type of cross-sectional shape, non-limiting examples of which include elliptical and oval.

FIG. 4 is a cross-section illustration of example manipulator device as described with reference to FIG. 1A-E where an inner cavity is surrounded by an inner tube, inner tube is surrounded by an outer tube and outer tube is surround by a tubular sheath.

Figure 5:
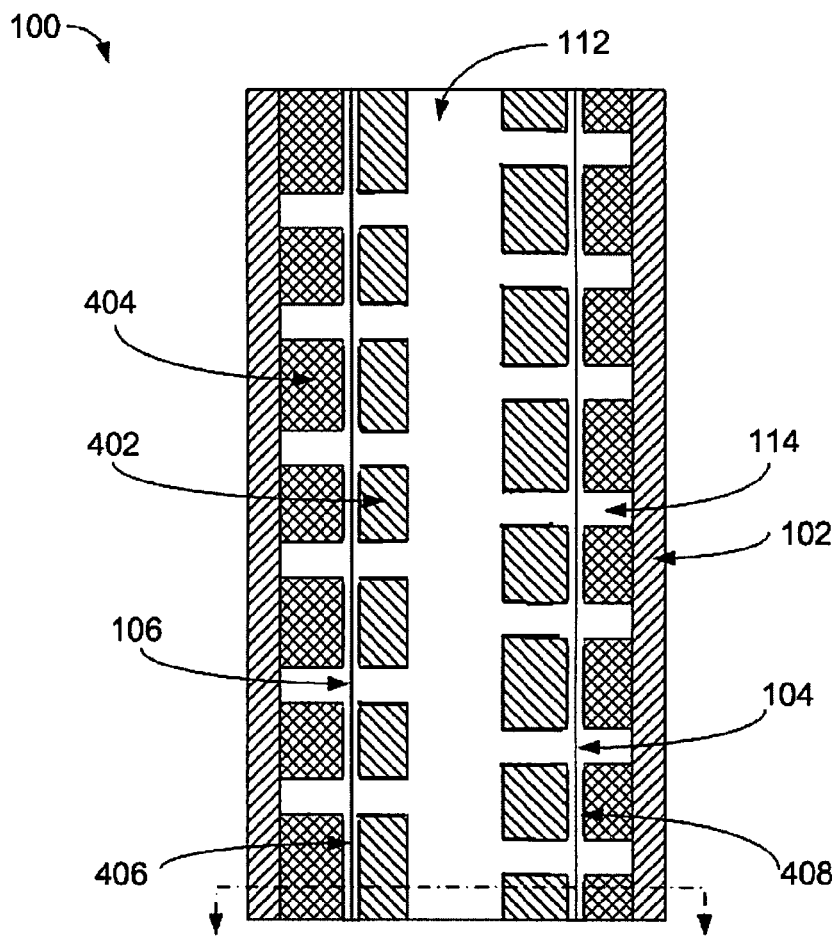
FIG. 5 is a cross-section illustration of example manipulator device as described with reference to FIG. 1A-E, in accordance with an embodiment of the present invention.
Figure 5:
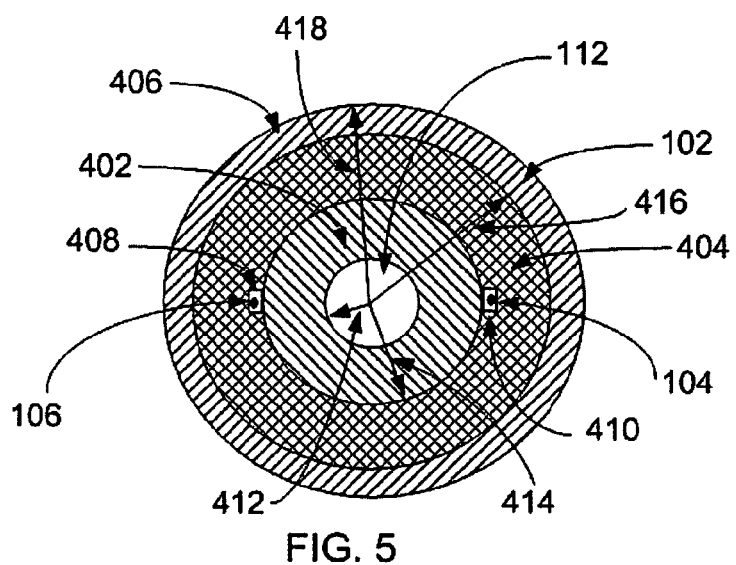

FIG. 5 is a cross-section illustration of example manipulator device as described with reference to FIG. 1A-E, in accordance with an exemplary embodiment of the present invention.

As compared to FIG. 4, spacing 408 and spacing 410 are located external to radius 414 and are contained within outer tube portion 404. As compared to FIG. 4 notch 114 extends partially through inner tube portion 402 and throughout outer tube portion 404. The location of spacing 408 and spacing 410 may be configured in different locations with respect to inner tube portion 402 and outer tube portion 404. The location of notch 114 may be configured in different locations with respect to inner tube portion 402 and outer tube portion 404. The configuration of spacings and notches may be manipulated in order to achieve various levels of flexibility and control.

Figure 6:
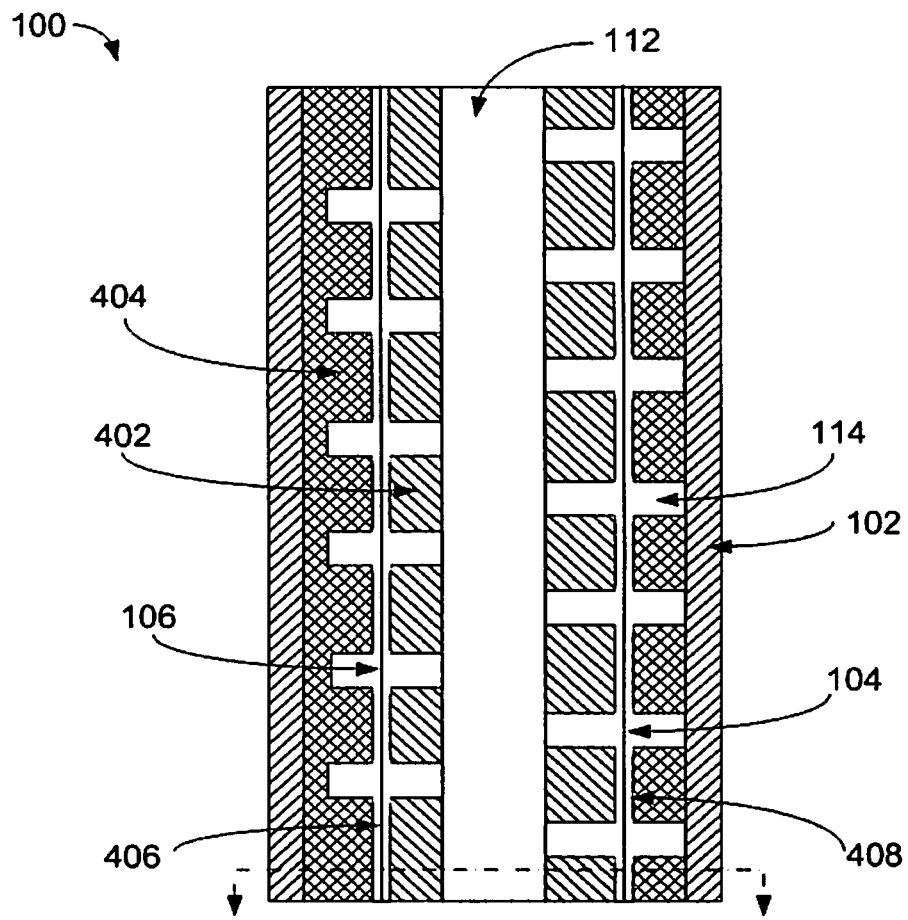
FIG. 6 is a cross-section illustration of example manipulator device as described with reference to FIG. 1A-E, in accordance with an embodiment of the present invention.
Figure 6:
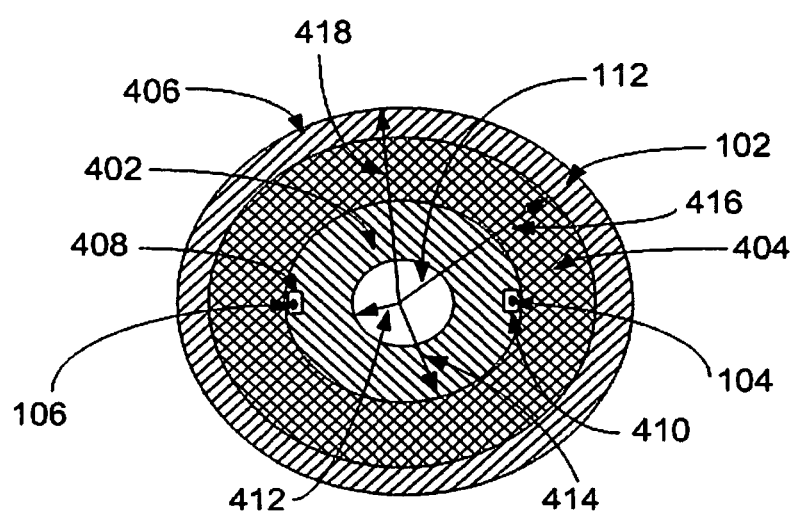

FIG. 6 is a cross-section illustration of example manipulator device as described with reference to FIG. 1A-E, in accordance with an exemplary embodiment of the present invention.

As compared to FIG. 4, spacing 408 and spacing 410 are located at a dimension less than radius 414. Furthermore, spacing 408 and spacing 410 are located within inner tube portion 402. The configuration of spacings may be manipulated in order to achieve various levels of flexibility and control.

Figure 7:
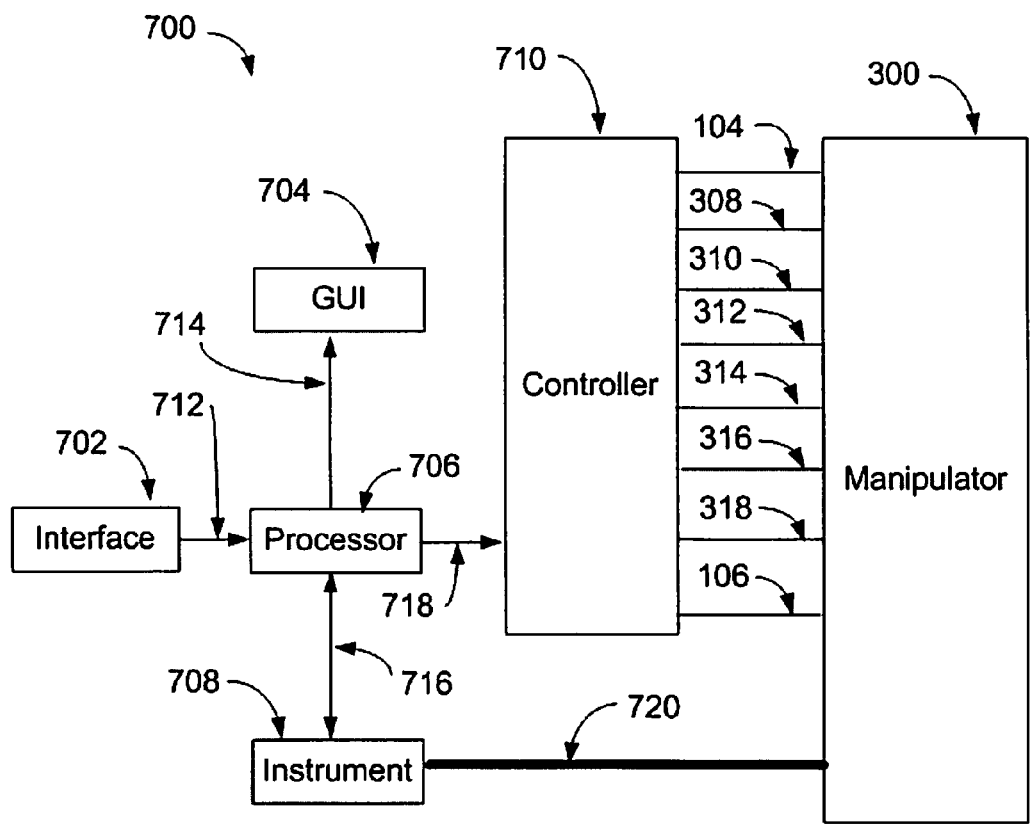
FIG. 7 is an illustration of an example system, in accordance with another embodiment of the present invention.

FIG. 7 is an illustration of an example system 700, in accordance with an exemplary embodiment of the present invention.

System 700 includes manipulator device 300, an interface portion 702, a GUI portion 704, a processor portion 706, an instrument portion 708 and a controller portion 710. In some embodiments, at least two of manipulator device 300, interface portion 702, GUI portion 704, processor portion 706, instrument portion 708 and controller portion 710 may be combined as a unitary device. In other embodiments, at least one of interface portion 702, GUI portion 704, processor portion 706, instrument portion 708 and controller portion 710 may be implemented as a computer having stored therein tangible computer-readable media for carrying or having computer-executable instructions or data structures stored thereon. Such tangible computer-readable media can be any available media that can be accessed by a general purpose or special purpose computer. Non-limiting examples of tangible computer-readable media include physical storage and/or memory media such as RAM, ROM, EEPROM, CD-ROM or other optical disk storage, magnetic disk storage or other magnetic storage devices, or any other medium which can be used to carry or store desired program code means in the form of computer-executable instructions or data structures and which can be accessed by a general purpose or special purpose computer. When information is transferred or provided over a network or another communications connection (either hardwired, wireless, or a combination of hardwired or wireless) to a computer, the computer properly views the connection as a computer-readable medium. Thus, any such connection is properly termed a tangible computer-readable medium. Combinations of the above should also be included within the scope of tangible computer-readable media.

Manipulator device 300 is arranged to receive control wires 104, 106, 308, 310, 312, 314, 316 and 318 from controller portion 710.

Processor portion 706 is arranged to receive information from interface portion 702 via a communication channel 712. GUI portion 704 is arranged to receive information from processor portion 706 via a communication channel 714. Processor portion 706 is arranged to communicate bi-directionally with instrument portion 708 via a communication channel 716. Controller portion 710 is arranged to receive information from processor portion 706 via a communication channel 718. Manipulator device 300 is arranged to receive an instrument device 720 from instrument portion 708. Non-limiting examples for instrument device include imaging instrument, cauterizing instrument, cutting instrument, material delivery instrument Manipulator device 300 operates as described previously with reference to FIG. 3.

Interface portion 702 receives input from a user (not shown). Non-limiting examples of devices which may be configured for interface portion 702 include joystick, mouse, trackball and motion detection device.

GUI portion 704 presents information for viewing by a user. Processor portion 706 receives and processes information for controlling the operation of system 700. Instrument portion 708 provides communication and control of an instrument device. Controller portion 710 controls the amount of force applied to control wires based upon received information. As a non-limiting example, controller portion 710 may be configured as a multiplicity of stepper motors.

In operation, manipulator device 300 is inserted into an opening. As an example, manipulator device 300 is inserted into an opening associated with a human body. Instrument device 720 traverses manipulator device 300 and may provide feedback information to processor portion 706 via instrument portion 708 and communication channel 716.

Processor portion 706 may present feedback information to GUI portion 704 via communication channel 714. Furthermore, the user may view feedback information presented via GUI portion 704. As an example, an optical instrument may be inserted into a human body for examining the internal tissues of the body. The observations of the internal tissue may be communicated to the user. Based upon received feedback information, the user may communicate configuration information to interface portion 702.

Configuration information may be communicated to processor portion 706 via communication channel 712. Processor portion 706 receives and processes configuration information and communicates control information to controller portion 710 via communication channel 718.

Controller portion 710 receives control information and modifies forces applied to control wires 104, 106, 308, 310, 312, 314, 316 and 318. Modification of forces applied to control wires modifies the flex or bending of manipulator device 300. For example, after insertion of the manipulator device into a human body, the user may observe an area of tissue to be examined with increased detail and may configure manipulator device such that the tissue may be observed with increased detail. The user may control other instruments via instrument portion 708 as needed. For example, a portion tissue may need to be removed and the user may insert a cutting instrument into the manipulator device for cutting the tissue. Furthermore, the user may insert a clamping instrument into the manipulator device for removing the separated tissue.

Figure 8:
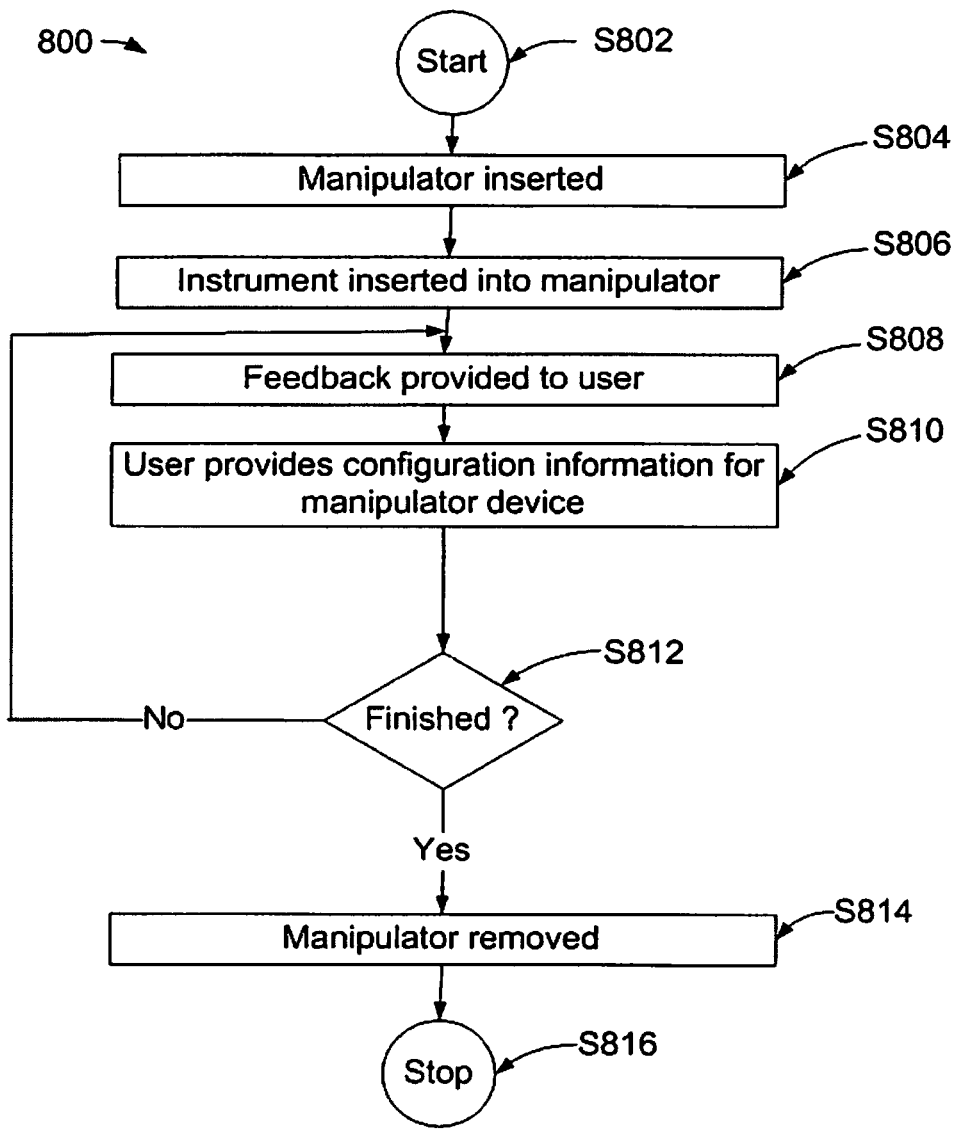
FIG. 8 illustrates an example method for the operation of the system, in accordance with still another embodiment of the present invention.

FIG. 8 illustrates an example method 800 for the operation of a system, in accordance with an exemplary embodiment of the present invention.

Method 800 starts (S802) and then the manipulator device is inserted (S804). For example, with reference to FIG. 3, manipulator device 300 is inserted into an opening. As an example, manipulator device 300 may be inserted through an opening in a human body.

An instrument may then be inserted through manipulator device (S806). For example, with reference to FIG. 3 and FIG. 7, instrument device 720 may be inserted through tubular cavity 332. In an example embodiment, an endoscope may be inserted into manipulator device 300 internally observe a patient.

Information associated with instrument may then be provided to a user (S808). For example, with reference to FIG. 7, then instrument device 720 provides information to user via instrument portion 708, communication channel 716, processor portion 706 and GUI portion 704. In an example embodiment, internal image information associated with tissues for a human body is provided to a user for viewing.

The user may then provide configuration information to the system (S810). For example, with reference to FIG. 7, the user provides configuration information to interface portion 702. Configuration information is communicated to processor portion 706 via communication channel 712. Processor portion 706 receives and processes configuration information. Processor portion 706 communicates control information to controller portion 710 via communication channel 718. Controller portion 710 receives control information and modifies forces applied to control wires. Forces applied to control wires modify the configuration (e.g. bend or flex) of manipulator device 300. As an example, a user moves a joystick in order to experience a better view of a tissue image provided by an optical instrument located internal to a human body.

It is then determined whether the procedure is complete (S812). For example, a user determines may determine whether additional configuration information is to be applied to system. In an example embodiment, a user may need to move the manipulator to a new position within the patient.

If it is determined that the procedure is not complete, information is again provided to user (S808).

Alternatively, if it is determined that the procedure is complete, then the manipulator device is removed (S814). For example, with reference to FIG. 7, user provides configuration information to interface portion 702 for removing manipulator device 300. After performing a minimally invasive surgical procedure, the manipulator device is removed from the patient. Method 800 then stops (S816).

Figure 9:
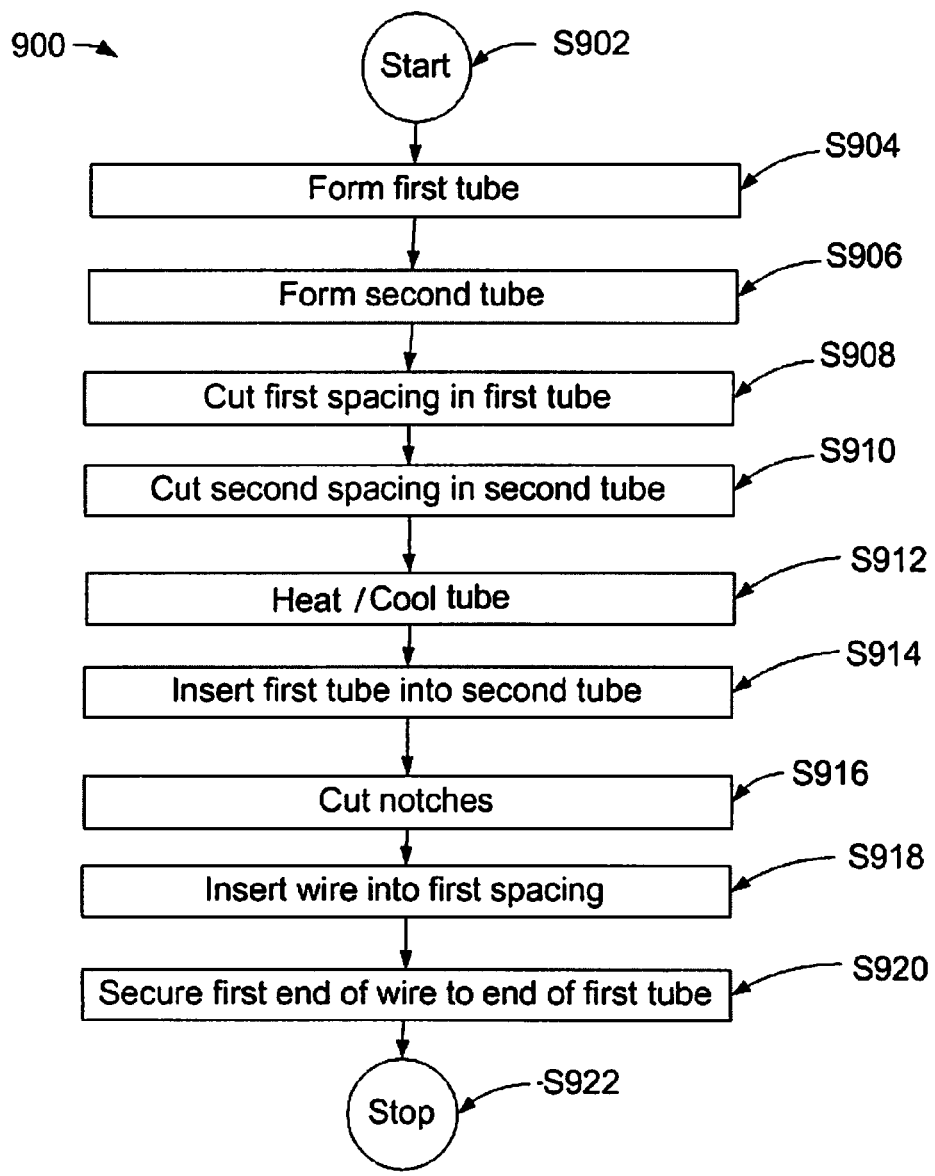
FIG. 9 illustrates an example method for fabricating a manipulator device, in accordance with yet another embodiment of the present invention.

FIG. 9 illustrates an example method 900 for fabricating a manipulator device, in accordance with an exemplary embodiment of the present invention.

Method 900 starts (S902) and a first tube is formed (S904). For example, a flexible material may be fashioned in a tubular shape as illustrated by inner tube portion 402 with reference to FIG. 4. As an example, a flat piece of elastic material may be rolled around a tubular device in order to form a tube. In another example, a tube may be formed by any known extrusion process, wherein the elastic material is drawn through a ring-shaped opening.

Then a second tube is formed (S906). For example, flexible material may be fashioned in a tubular shape as illustrated by outer tube portion 404 with reference to FIG. 4. As an example, a flat piece of elastic material may be rolled around a tubular device in order to form a tube. In some examples, outer tube portion 104 is the same material as inner tube portion 402. In other examples, outer tube portion 104 is a different material from inner tube portion 402.

At this point, spacing is providing into one of the tubes (S908). For example, a first spacing is cut in the outer perimeter of inner tube portion 402 as described with reference to FIG. 4. Furthermore, first spacing traverses the length of inner tube portion 402. As will be described in a later paragraph, a portion of the first spacing may form spacing 408 as described with reference to FIG. 4.

Then a second spacing is provided into one of the tubes (S910). For example, second spacing is cut in the inner diameter of outer tube portion 404 as described with reference to FIG. 4. Furthermore, second spacing traverses the length of outer tube portion 404. As will be described in further detail below, a portion of the second spacing may form spacing 408 as described with reference to FIG. 4.

In some embodiments, both spacings are provided in the same tube. Further, in some embodiments, the spacing may traverse the entire thickness of one of the tubes.

This portion of method 900 is optional, in the sense that a second control wire (which will ultimately be inserted into the second spacing) may not be needed. Further, this portion may be repeated in some embodiments, in the sense that more than two control wires (which will ultimately be inserted into the more than two spacings, respectively) may be needed.

Referring to FIG. 9, one of the tubes are cooled/heated (S912). In an example embodiment, to make a tight fit of inner tube portion 402 and outer tube portion 404, inner tube portion 402 and outer tube portion 404 start with the same diameters. Then inner tube portion 402 is cooled. Cooling inner tube portion 402 shrinks or reduces the physical size of the tube. In another example embodiment, to make a tight fit of inner tube portion 402 and outer tube portion 404, outer tube portion 402 is heated. Heating inner tube portion 402 expands the physical size of the outer tube portion. In yet another example embodiment, to make a tight fit of inner tube portion 402 and outer tube portion 404, inner tube portion 402 is cooled and outer tube portion 402 is heated.

At this point, the first tube is inserted into second tube (S914). For example, inner tube portion 402 is inserted into outer tube portion 404. In one embodiment, as a result of shrinking inner tube portion 402 via cooling, inner tube portion 402 fits within outer tube portion 404. In another embodiment, as a result of expanding outer tube portion 404 via heating, inner tube portion 402 fits within outer tube portion 404. In another embodiment, as a result of shrinking inner tube portion via cooling and expanding outer tube portion 404 via heating, inner tube portion 402 fits within outer tube portion 404. Inner tube portion 402 and out tube portion 404 then return to original temperature, thus expanding/cooling to their original dimensions, respectively.

In yet another embodiment, to make a tight fit of inner tube portion 402 and outer tube portion 404, inner tube portion 402 has a slightly smaller diameter that that of outer tube portion 404. In this case, no heating or cooling (no S912) is required to insert inner tube portion 402 into outer tube portion 404.

Notches may then be cut into the tube assembly (S916). For example, notches (such as notch 114 as described with reference to FIGS. 1A-D and FIGS. 4-6) are cut into tube assembly 102. Any known cutting system or method may be used to cut notches, non-limiting examples of which include a precision laser cutting tool and a wire electron discharge machining tool.

A wire may then be inserted into the notched tube assembly (S918). For example, control wire 104 as described with reference to FIG. 1 is inserted into the spacing associated with inner tube portion 402 as described with reference to FIG. 4. Control wire 104 may be secured via termination device 108 (e.g. knot) as described with reference to FIG. 2.

A wire may then inserted into second spacing (S914). For example, a first end of control wire 106 as described with reference to FIG. 1 is secured with respect to outer tube portion 404 as described with reference to FIG. 4. Control wire 106 may be secured via termination device 110 (e.g. knot) as described with reference to FIG. 2.

This portion of method 900 additionally is optional, in the sense that a second control wire may not be needed. Further, this portion may additionally be repeated in some embodiments, in the sense that more than two control wires may be needed. Method 900 then stops (S922).

The present invention provides a manipulator that is easy to fabricate. The manipulator may be used for minimally-invasive surgical procedures. The manipulator may controlled to bend at multiple points, to rotate, pivot and move in a direction along its length. In short, the present invention provides highly controllable, yet simple to manufacture manipulator.

The foregoing description of various preferred embodiments of the invention have been presented for purposes of illustration and description. It is not intended to be exhaustive or to limit the invention to the precise forms disclosed, and obviously many modifications and variations are possible in light of the above teaching. The example embodiments, as described above, were chosen and described in order to best explain the principles of the invention and its practical application to thereby enable others skilled in the art to best utilize the invention in various embodiments and with various modifications as are suited to the particular use contemplated. As such, it will be understood that various modifications may be made to the embodiments disclosed herein. Therefore, the above description should not be construed as limiting the scope of the invention, but merely as illustrating exemplifications of preferred embodiments. Those skilled in the art will readily envision other modifications within the scope and spirit of the present invention as defined by the appended claims

What is claimed is:

1. A medical device comprising:
    a first tube comprising a first sheet of a first material having elasticity;
    a second tube comprising a second sheet of a second material having elasticity,
    a first control wire, and
    a second control wire,
    wherein said first sheet of said first material has a first thickness and a first length and is formed to have a first cross-section having a first inner periphery and a first outer periphery,
    wherein said second sheet of said second material has a second thickness and a second length and is formed to have a second cross-section having a second inner periphery and a second outer periphery,
    wherein a first spacing is disposed in said first sheet of said first material or said second sheet of said second material between the first sheet and second sheet along the first length or the second length, respectively,
    wherein a second spacing is disposed in said first sheet of said first material or said second sheet of said second material between the first sheet and second sheet along the first length or the second length, respectively, said second spacing being positioned on an opposite side of the device relative to the first spacing,
    wherein said first outer periphery is substantially equal to said second inner periphery to provide a tight fit between the first and second sheets, wherein said second sheet of said second material surrounds said first sheet of said first material, wherein said first control wire and said second control wire each have an end fixed to one of said first sheet of said first material and said second sheet of said second material, and wherein said first control wire is disposed within the first spacing and said second control wire is disposed within the second spacing, wherein the first sheet of said first material has a first plurality of flex notches disposed along the first length and the second sheet of said second material has a second plurality of flex notches disposed along the second length, wherein notches of the first plurality of flex notches extend only partially through the first sheet and notches of the second plurality of flex notches extend through the second sheet.

2. The medical device of claim 1, further comprising a deformable sheathing disposed around said second sheet of said second material.

3. The medical device of claim 1, wherein the first cross-section is elliptical.

4. The medical device of claim 1, wherein the first cross-section is oval.

5. The medical device of claim 1, wherein the first material comprises nitinol.

6. The medical device of claim 1, wherein said first material has shape memory.

7. The medical device of claim 1, wherein the first plurality of flex notches is at least partially aligned with the second plurality of flex notches.

8. The medical device of claim 1, wherein the first plurality of flex notches and second plurality of flex notches have a uniform height dimension when the device is not bent, and in response to bending the device, the height dimension of at least a portion of the first plurality of flex notches and second plurality of flex notches is not uniform.

9. The medical device of claim 1 further comprising:
a third control wire disposed between the first control wire and the second control wire, wherein said application of a force to the first control wire causes the device to bend in a first direction, application of a force to the second control wire causes the device to bend in a second direction, and application of force to the third control wire causes the device to bend in a third direction.

10. The medical device of claim 9, wherein an end of the third control wire is fixed at a third length which is shorter than the first length or the second length.

11. A system comprising:
a device comprising:
a first tube comprising a first sheet of a first material,
a second tube comprising a second sheet of a second material,
a first control wire, and
a second control wire,
said first sheet of said first material having elasticity, said second sheet of said second material having elasticity; and
a controller,
wherein said first sheet of said first material has a first thickness and a first length and is shaped so as to have a first cross-section having a first inner periphery and a first outer periphery,
wherein said second sheet of said second material has a second thickness and a second length and is shaped so as to have a second cross-section having a second inner periphery and a second outer periphery, wherein a first spacing is disposed in said first sheet of said first material or said second sheet of said second material between the first sheet and second sheet along the first length or the second length, respectively, wherein a second spacing is disposed in said first sheet of said first material or said second sheet of said second material between the first sheet and second sheet along the first length or the second length, respectively, said second spacing being positioned on an opposite side of the device relative to the first spacing, wherein said first outer periphery is substantially equal to said second inner periphery to provide a tight fit between the first and second sheets, wherein said second sheet of said second material surrounds said first sheet of said first material, wherein said first control wire and said second control wire each have a first end and a second end, each of said first ends being fixed to one of said first sheet of said first material and said second sheet of said second material, said second ends being attached to said controller, and wherein said first control wire is disposed within the first spacing and said second control wire is disposed within the second spacing, wherein the first sheet of said first material has a first plurality of flex notches disposed along the first length and the second sheet of said second material has a second plurality of flex notches disposed along the second length, wherein notches of the first plurality of flex notches extend only partially through the first sheet and notches of the second plurality of flex notches extend through the second sheet.

12. The medical system of claim 11, further comprising one of an imaging instrument, a cauterizing instrument, a cutting instrument and x material delivery instrument disposed within said device.

13. The medical system of claim 11, wherein said controller performs at least one of rotating said device about an axis parallel to the first length, moving said device in a direction of the first length, pivoting said device about a pivot point and pulling said first control wire.

14. The medical system of claim 11, wherein said first material has shape memory.

15. A method of making a medical device comprising:
forming a first tube comprising of a first sheet from a first material having a first thickness, a first cross-section, a first inner periphery, a first outer periphery and elasticity, the tube having a first length;
forming a second tube comprising of a second sheet from a second material having a second thickness, a second cross-section, a second inner periphery, a second outer periphery and elasticity, the second tube having a second length;
forming a first spacing in a first line in the first sheet or second sheet along the first length or second length, respectively;
forming a second spacing in a second line in the first sheet or second sheet along the first length or second length, respectively;
disposing the first tube within the second tube, wherein the first spacing and the second spacing are disposed between the first sheet and the second sheet;
disposing a first control wire in the first spacing and a second control wire in the second spacing, each control wire having an end; and fixing each end to one of the first tube and the second tube,
wherein said second spacing is positioned on an opposite side of the first tube relative to the first spacing, and
wherein said first outer periphery is substantially equal to said second inner periphery to provide a tight fit between the first and second tubes,
wherein the first sheet of said first material has a first plurality of flex notches disposed along the first length and the second sheet of said second material has a second plurality of flex notches disposed along the second length, wherein notches the first plurality of flex notches extend only partially through the first sheet and notches of the second plurality of flex notches extend through the second sheet.

16. The method of making a medical device of claim 15, wherein said disposing the first tube within the second tube comprises:
cooling the first tube to contract the first cross section;
placing the first tube within the second tube; and
heating the first tube to expand the first cross section.

17. The method of making a medical device of claim 15, wherein said disposing the first tube within the second tube comprises: heating the second tube to expand the second cross section; placing the first tube within the second tube; and cooling the second tube to contract the second cross section.

18. The method of making a medical device of claim 15, wherein the first material has shape memory.

\* \* \* \* \*